(12) United States Patent
Jerome et al.

(10) Patent No.: US 8,247,392 B2
(45) Date of Patent: Aug. 21, 2012

(54) MATERIALS FOR SELECTIVE TRAPPING OF CARBON MONOXIDE

(75) Inventors: François Jerome, Dijon (FR); Géraud Dubois, Dijon (FR); Stéphane Brandes, Dijon (FR); Gabriel Canard, Dijon (FR); Jean-Michel Barbe, Brétigny (FR); Roger Guilard, Fontaine-les-Dijon (FR); Bruno Roux-Fouillet, Dijon (FR); Henry Ledon, Versailles (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 2037 days.

(21) Appl. No.: 10/485,935

(22) PCT Filed: Jul. 19, 2002

(86) PCT No.: PCT/FR02/02591
§ 371 (c)(1),
(2), (4) Date: Jul. 25, 2005

(87) PCT Pub. No.: WO03/011865
PCT Pub. Date: Feb. 13, 2003

(65) Prior Publication Data
US 2006/0287195 A1    Dec. 21, 2006

(30) Foreign Application Priority Data
Aug. 1, 2001  (FR) ...................................... 01 10317

(51) Int. Cl.
*C07D 487/22* (2006.01)
(52) U.S. Cl. .......................................... 514/63; 540/145
(58) Field of Classification Search .................... 540/145
See application file for complete search history.

(56) References Cited

U.S. PATENT DOCUMENTS 6,028,025 A * 2/2000 Ying et al. .................... 502/171

OTHER PUBLICATIONS

Jerome et al. First synthesis of sterically hindered cofacial bis(corroles) and their bis(cobalt) complexes. 1998, Chemical Communications, 18, 2007-2008.*

* cited by examiner

*Primary Examiner* — James O Wilson
*Assistant Examiner* — Brian McDowell
(74) *Attorney, Agent, or Firm* — Young & Thompson

(57) ABSTRACT

Compounds of formula (I) are disclosed.

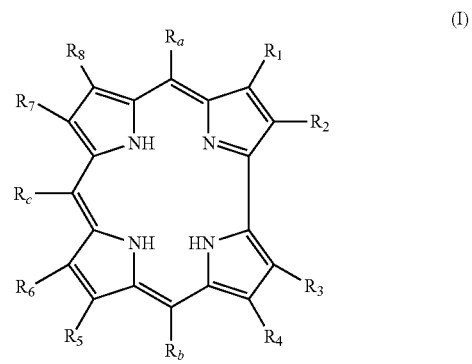

The tetrapyrole ring in formula (I) can be substituted with a metal cation (M); $R_1$, $R_2$, $R_3$ and $R_4$ separately represent a hydrogen atom, a C1-4 alkyl or alkyloxy radical, or a phenyl radical optionally substituted by vinyl, hydroxy, nitro, amino, bromo, chloro, fluoro, iodo, benzyloxy, or hydroxymethyl radicals; $R_5$, $R_6$, $R_7$ and $R_8$ separately represent a hydrogen atom or a C1-4 alkyl radical; $R_a$, $R_b$ and $R_c$ separately represent a hydrogen atom, a C1-4 alkyl or alkyloxy radical optionally substituted by a halogen, or a phenyl radical optionally substituted by vinyl, hydroxy, nitro, amino, bromo, chloro, fluoro, iodo, benzyloxy, or hydroxymethyl radicals, wherein at least one of $R_a$, $R_b$, and $R_c$ is a phenyl radical. Compounds of formula (I) bound to a silica, a sol-gel material or a mesoporous silica are useful for selective trapping of carbon monoxide.

10 Claims, 13 Drawing Sheets

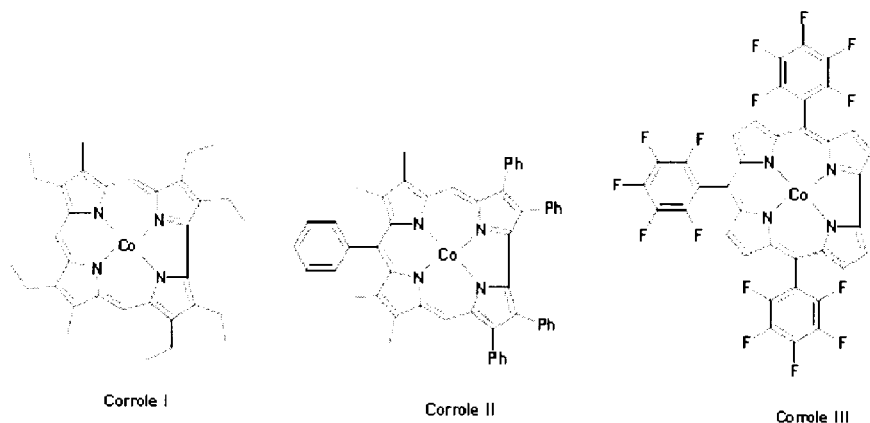
Figure 8
Electron density on the Co**     Corrole I > Corrole II > Corrole III
Affinity expected for CO     Corrole III > Corrole II > Corrole I
Figure 9
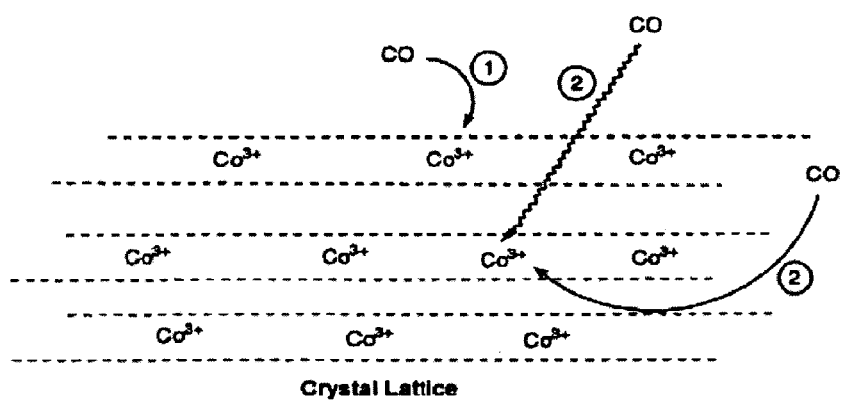
Figure 10

Corrole IV

MATERIALS FOR SELECTIVE TRAPPING OF CARBON MONOXIDE

BACKGROUND OF THE INVENTION

1. Field of the Invention

A subject matter of the invention is novel compounds capable of complexing carbon monoxide and their use in detectors for said gas.

2. Related Art

Semi-conducting metal oxides, such as ZnO, $TiO_2$, $SnO_2$, $WO_3$ or $Ga_2O_3$, are very widely used as active supports for detectors for carbon monoxide. The essential characteristic of these compounds is their high sensitivity for carbon monoxide; however, their operating temperature is high (=350° C.).

Other metal oxides, those having a perovskite structure ($ABO_3$, where A and B are different metals), have been tested for detecting carbon monoxide. These compounds have good sensitivity for this gas with lower operating temperatures, of the order of 150-200° C.

Hemoglobin, myoglobin and their models are capable of coordinating oxygen and carbon monoxide in solution at ambient temperature. This coordination occurs at the iron (II) atom of the hemoprotein. For this type of compound, the selectivity for one or other of the gases is given by M, which is the ratio of the partial pressures at half-saturation of the two gases[1].

$$M=P_{1/2}O_2/P_{1/2}CO$$

A high value of M reflects a greater affinity for carbon monoxide than for oxygen.

Myoglobin, for which M is between 20 and 40, and hemoglobin, for which M is approximately equal to 150, have a high affinity for oxygen at ambient temperature.

On the other hand, the compound known as (To-PivPP) Fe ($1,2Me_2Im$) and represented by FIG. 1, for which the value M in solution at ambient temperature is of the order of 4 000 with a carbon monoxide half-saturation partial pressure ($P_{1/2}CO$) approximately equal to $9\times10^{-3}$ Torr (1 Torr=1 mm Hg=$10^5$ Pa/760), has more affinity for carbon monoxide than for oxygen at ambient temperature. However, the long-term stability of compounds of this type is limited, in particular because of the oxidation of iron(II) to iron(III) in air in the presence of moisture, which then inhibits any subsequent coordination of carbon monoxide.

SUMMARY OF THE INVENTION

In the light of the information given in the literature, there exists a need for compounds which are capable of selectively and reversibly coordinating carbon monoxide at ambient temperature and which exhibit great stability over time. Among the possible candidate macrocycles, the inventors have been interested in corrole, represented by FIG. 2. This is a tetrapyrrole, like the porphyrins[2]. In contrast to the porphyrins, corrole has three carbon atoms bridging two pyrrole units instead of four. This ring contraction confers noteworthy properties on the corroles. This is because the macrocyclic cavity is smaller in size than that of the porphyrins and the three amine functional groups allow it to stabilize metals in higher degrees of oxidation.

For this reason, a subject matter of the invention is a compound of formula (I):

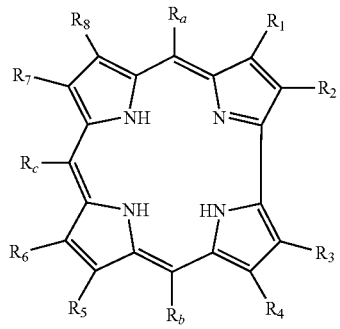

in which:

$R_1$, $R_2$, $R_3$ and $R_4$, which are identical or different, represent, independently of one another, a hydrogen atom, a linear or branched alkyl radical comprising from 1 to 4 carbon atoms, an unsubstituted phenyl radical or a phenyl radical substituted by one or more identical or different groups chosen, independently of one another, from vinyl, hydroxyl, nitro, amino, bromo, chloro, fluoro, iodo or benzyloxy radicals, linear or branched alkyl radicals comprising from 1 to 4 carbon atoms or linear or branched alkyloxy radicals comprising from 1 to 4 carbon atoms, said alkyl and alkyloxy radicals themselves being either unsubstituted or substituted by one or more bromo, chloro, fluoro or iodo groups;

$R_5$, $R_6$, $R_7$ and $R_8$, which are identical or different, represent, independently of one another, a hydrogen atom or a linear or branched alkyl radical comprising from 1 to 4 carbon atoms;

$R_a$, $R_b$ and $R_c$, which are identical or different, represent, independently of one another, a hydrogen atom, an unsubstituted phenyl radical or a phenyl radical substituted by one or more identical or different groups chosen, independently of one another, from vinyl, hydroxyl, nitro, amino, bromo, chloro, fluoro, iodo or benzyloxy radicals, linear or branched alkyl radicals comprising from 1 to 4 carbon atoms or linear or branched alkyloxy radicals comprising from 1 to 4 carbon atoms, said alkyl and alkyloxy radicals themselves being either unsubstituted or substituted by one or more bromo, chloro, fluoro or iodo groups.

The term "linear or branched alkyl radical comprising from 1 to 4 carbon atoms" denotes one of the methyl, ethyl, propyl, isopropyl, butyl, 1-methylpropyl, 2-methylpropyl or 1,1-dimethylethyl radicals.

The term "linear or branched alkyloxy radical comprising from 1 to 4 carbon atoms" denotes one of the methoxy, ethoxy, propoxy, isopropoxy, butoxy, 1-methylpropoxy, 2-methylpropoxy or 1,1-dimethylethoxy radicals.

The term "phenyl radical substituted by one or more identical or different groups chosen, independently of one another, from vinyl, cyano, carboxyl, hydroxyl, nitro, amino, bromo, chloro, fluoro, iodo or benzyloxy radicals, linear or branched alkyl radicals comprising from 1 to 4 carbon atoms or linear or branched alkyloxy radicals comprising from 1 to 4 carbon atoms, said alkyl and alkyloxy radicals themselves being either unsubstituted or substituted by one or more bromo, chloro, fluoro or iodo groups" denotes, for example, the 2,3,4,5,6-pentafluorophenyl, 2-fluorophenyl, 2-bromophenyl, 2-cyanophenyl, 2-carboxyphenyl, 2-chlorophenyl, 2-iodophenyl, 2-nitrophenyl, 2-methoxyphenyl, 2-hydroxyphenyl, 2-aminophenyl, 2-(hydroxymethyl)phenyl, 2-vinylphenyl, 2-(methoxymethyl)phenyl, 3-fluorophenyl, 3-bromophenyl, 3-cyanophenyl, 3-carboxyphenyl, 3-chlorophenyl, 3-iodophenyl, 3-nitrophenyl, 3-methoxyphenyl, 3-hydroxyphenyl, 3-aminophenyl, 3-(hydroxymethyl)phenyl, 3-vinylphenyl, 3-(methoxymethyl)phenyl, 4-fluorophenyl, 4-bromophenyl, 4-cyanophenyl, 4-carboxyphenyl, 4-chlorophenyl, 4-iodophenyl, 4-nitrophenyl, 4-methoxyphenyl, 4-hydroxyphenyl, 2-tolyl, 3-tolyl or 4-tolyl, 3,4-xylyl, 3,4-dimethoxyphenyl, 3,4-dichlorophenyl, 4-aminophenyl, 4-(hydroxymethyl)phenyl, 4-vinylphenyl or 4-(methoxymethyl)phenyl radicals.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein:

FIG. 8 illustrates three cobalt complexes (Corrole I, Corrole II, and Corrole III) chosen as examples for the study;

FIG. 9 illustrates the affinity of the three cobalt complexes for carbon monoxide;

FIG. 10 illustrates the two Langmuir isotherms for the adsorption of carbon monoxide by cobalt complexes;

DESCRIPTION OF PREFERRED EMBODIMENTS

Figure 1:
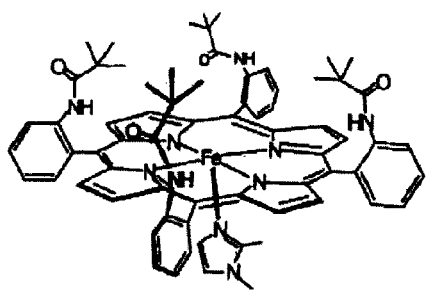
FIG. 1 illustrates the molecular structure of the compound (To-PivPP) Fe (1,2 Me$_2$Im) complex.
Figure 2:
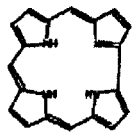
FIG. 2 illustrates the molecular structure of the compound corrole macrocycle.

According to a first specific aspect, a subject matter of the invention is a compound of formula (I) as defined above in which just one of the $R_a$, $R_b$ or $R_c$ groups represents an unsubstituted phenyl radical or a phenyl radical substituted by one or more identical or different groups chosen, independently of one another, from vinyl, hydroxyl, nitro, cyano, carboxyl, amino, bromo, chloro, fluoro, iodo or benzyloxy radicals, linear or branched alkyl radicals comprising from 1 to 4 carbon atoms or linear or branched alkyloxy radicals comprising from 1 to 4 carbon atoms, said alkyl and alkyloxy radicals themselves being either unsubstituted or substituted by one or more bromo, chloro, fluoro or iodo groups.

According to a second specific aspect, a subject matter of the invention is a compound of formula (I) as defined above in which just one of the $R_a$, $R_b$ or $R_c$ groups represents a radical chosen from the 4-bromophenyl, 4-chlorophenyl, 4-iodophenyl, 4-nitrophenyl, 4-cyanophenyl, 4-carboxyphenyl, 4-hydroxyphenyl, 4-aminophenyl, 4-(hydroxymethyl)phenyl or 4-vinylphenyl radicals and the other two groups from $R_a$, $R_b$ or $R_c$ each represent a hydrogen atom.

According to a third specific aspect, a subject matter of the invention is a compound of formula (I) as defined above in which $R_a$ and $R_b$ each represent a hydrogen atom.

According to a fourth specific aspect, a subject matter of the invention is a compound of formula (I) as defined above in which either $R_a$ and $R_c$ or $R_b$ and $R_c$ each represent a hydrogen atom.

According to a fifth specific aspect of the present invention, the three groups $R_a$, $R_b$ and $R_c$ each represent a hydrogen atom.

According to a sixth specific aspect, a subject matter of the invention is a compound of formula (I) as defined above in which $R_1$, $R_2$, $R_3$ and $R_4$, which are identical or different, represent, independently of one another, an unsubstituted phenyl radical or a phenyl radical substituted by one or more identical or different groups chosen, independently of one another, from vinyl, hydroxyl, nitro, amino, cyano, carboxyl, bromo, chloro, fluoro, iodo or benzyloxy radicals, linear or branched alkyl radicals comprising from 1 to 4 carbon atoms or linear or branched alkyloxy radicals comprising from 1 to 4 carbon atoms, said alkyl and alkyloxy radicals themselves being either unsubstituted or substituted by one or more bromo, chloro, fluoro or iodo groups.

According to a seventh specific aspect, a subject matter of the invention is a compound of formula (I) as defined above in which $R_5$, $R_6$, $R_7$ and $R_8$, which are identical or different, represent, independently of one another, a linear or branched alkyl radical comprising from 1 to 4 carbon atoms and more particularly a methyl radical or an ethyl radical.

According to an eighth specific aspect, a subject matter of the invention is a compound of formula (I) as defined above in which $R_5$, $R_6$, $R_7$ and $R_8$ are identical and each represent a methyl radical or an ethyl radical.

According to a ninth specific aspect, a subject matter of the invention is a compound of formula (I) as defined above in which $R_1$, $R_2$, $R_3$ and $R_4$ are identical and each represent a phenyl radical.

Another subject matter of the invention is a compound of formula (II):

$$G(Y)_a,$$

in which G represents an organometallic cation of formula (II'):

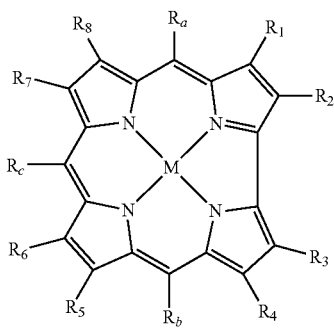

in which:

$R_1$, $R_2$, $R_3$, $R_4$, $R_5$, $R_6$, $R_7$, $R_8$, $R_a$, $R_b$ and $R_c$ are as defined above and M represents a metal cation chosen from the cobalt (Co), rhodium (Rh), iridium (Ir), manganese (Mn), iron (Fe), ruthenium (Ru) and osmium (Os) ions, Y represents an organic or inorganic anion and α represents an integer or decimal number so that the compound of formula (II) is electrically neutral.

Y is chosen from the anions conventionally used in the chemistry of organometallic complexes and more particularly from the chloride, bromide, iodide, acetate, trifluoroacetate, propionate, benzoate, trifluoromethylsulfonate, mesylate, benzenesulfonate, tosylate or tetrafluoroborate anions.

According to a tenth specific aspect of the present invention, a subject matter of the latter is an organometallic complex, the cationic part of which is represented by the formula (II') as defined above in which M represents a metal cation chosen from Fe(III) and Co(III).

Another subject matter of the invention is a silica modified by a compound of formula (I) or of formula (II) as defined above in which at least one of the $R_a$, $R_b$ or $R_c$ groups represents an unsubstituted phenyl radical or a substituted phenyl radical, characterized in that the spacer arms which make possible the anchoring of the molecules of formulae (I) or of the cations of formulae (II') to silica gel are, on the one hand, bonded to said compounds via one of the 2-, 3- or 4-positions of one or more of the phenyl radicals represented by at least one of the $R_a$, $R_b$ or $R_c$ groups and, on the other hand, bonded to one or more of the free silanol functional groups of a silica gel via a covalent bond Si—O.

According to an eleventh specific aspect of the present invention, in the modified silica as defined above, the divalent radical connecting to the silicon atom participating in one or more covalent bonds Si—O and the 2-, 3- or 4-position of said phenyl radical is chosen from the following divalent radicals:

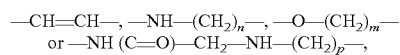

in which n, m and p, which are identical or different, represent, independently of one another, an integer greater than or equal to 0 and less than or equal to 4.

Another subject matter of the invention is a sol-gel material derived from a compound of formula (I) or from a compound of formula (II) as defined above in which the three $R_a$, $R_b$ and $R_c$ groups represent an unsubstituted phenyl radical or a substituted phenyl radical, characterized in that the 2-, 3- or 4-position of said phenyl radicals is substituted by a monovalent radical having an end group:

in which $R_{14}$ represents a methyl radical, an ethyl radical or an isopropyl radical.

According to a twelfth specific aspect of the present invention, a subject matter of the latter is a sol-gel material as defined above in which the monovalent radical having an end group —Si(OR$_{14}$)$_3$ is chosen from the following radicals:

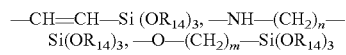

or

in which n, m and p, which are identical or different, represent, independently of one another, an integer greater than or equal to 0 and less than or equal to 4 and $R_{14}$ represents a methyl radical, an ethyl radical or an isopropyl radical.

Another subject matter of the invention is a mesoporous silica modified by a compound of formula (I) or of formula (II) as defined above in which at least one of the $R_a$, $R_b$ or $R_c$ groups represents an unsubstituted phenyl radical or a substituted phenyl radical, characterized in that the spacer arms which make possible the anchoring of the molecules of formulae (I) or of the cations of formulae (II') to silica gel are, on the one hand, bonded to said compounds via one of the 2-, 3- or 4-positions of just one or several of the phenyl radicals represented by at least one of the $R_a$, $R_b$ or $R_c$ groups and, on the other hand, bonded to one or more of the free silanol functional groups of the mesoporous silica via a covalent bond Si—O.

According to a thirteenth specific aspect of the present invention, in the modified mesoporous silica as defined above, the divalent radical connecting the silicon atom participating in one or more covalent bonds Si—O and the 2-, 3- or 4-position of said phenyl radical is chosen from the following divalent radicals:

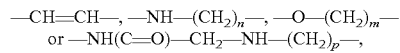

in which n, m and p, which are identical or different, represent, independently of one another, an integer greater than or equal to 0 and less than or equal to 4.

Another subject matter of the invention is a process for the separation of carbon monoxide from a gas mixture comprising it, characterized in that said mixture is brought into contact with either a compound of formula (II), or with a silica modified by a compound of formula (II), or with a sol-gel material of compound of formula (II), or with a mesoporous silica modified by a compound of formula (II), as defined above, so as to bring about the adsorption of the carbon monoxide on said compounds.

Such a process can be employed to detect the presence of carbon monoxide in a given atmosphere and more particularly in humid air.

It can also be employed to separate carbon monoxide from hydrogen in the processes in industrial chemistry which result in this mixture.

EXAMPLES

The following experimental part illustrates the invention without, however, limiting it.

1. Syntheses of the Ligand a)—Synthesis from a dipyrromethane

Figure 3:
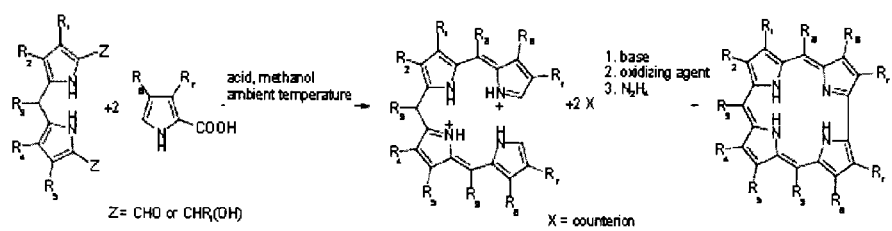
FIG. 3 illustrates the synthesis of corrole from macrocycle dipyrromethane.

The synthesis represented in FIG. 3 is carried out by condensation of two equivalents of carboxy-pyrrole with an appropriate dipyrromethane with acid catalysis. An intermediate of biladiene "a-c" type is easily obtained, which intermediate is cyclized under the action of a base before being subjected to an oxidation reaction in order to form the corrole.[3,4]

b)—Direct synthesis

Figure 4:
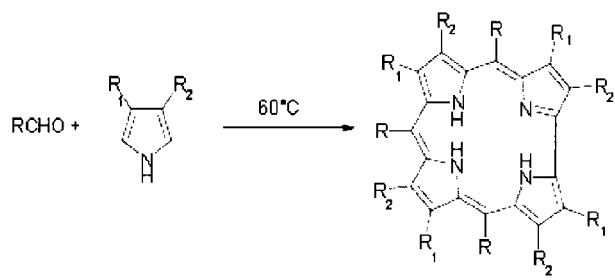
FIG. 4 illustrates the direct synthesis of corrole macrocycle complex.

Under some conditions, it is possible to directly synthesize the corrole macrocycle in a single stage. This reaction[5], represented in FIG. 4, is carried out without solvent and can be carried out in the presence of a solid support of alumina type.

c)—Synthesis by condensation of a dipyrromethane and of a dipyrryl sulfide

Figure 5:
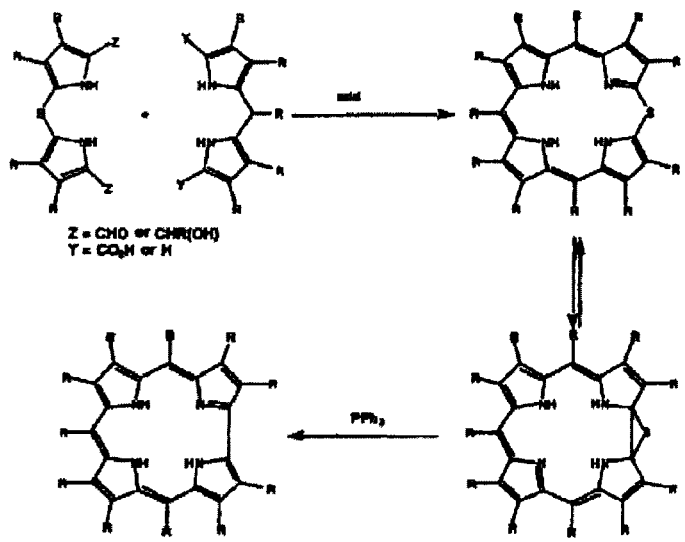
FIG. 5 illustrates the synthesis of corrole macrocycle by the condensation of the dipyrromethane and aipyrryl sulfide.

This method, represented in FIG. 5, consists in bringing together a dipyrromethane and a dipyrryl sulfide in methanol in an acidic medium[6]. The intermediate compound is a "meso" thiamacrocycle, the structure of which depends on the nature of the substituents in the β-pyrrole position. The extrusion of the sulfur can be obtained by thermolysis in dichlorobenzene and in the presence of triphenylphosphine. However, this synthetic route does not at present allow high yields of corrole to be obtained.

2. Metallation by Cobalt a)—Metallation of the corrole

Figure 6:
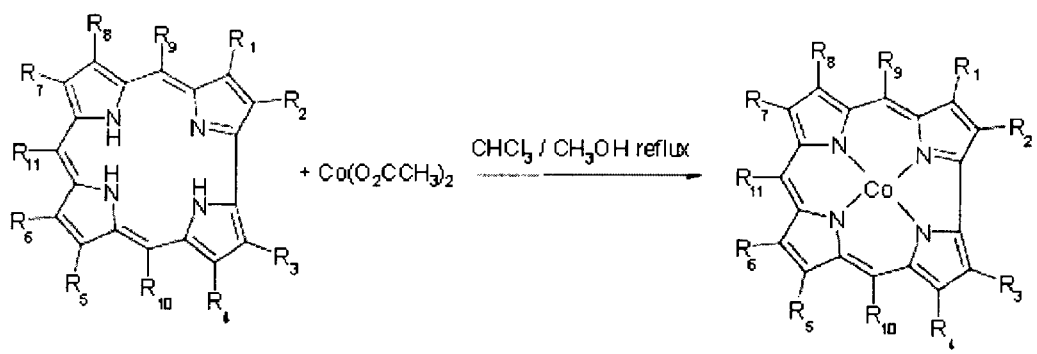
FIG. 6 illustrates the metallation of corrole macrocycle complex.

The metallation of the corrole, represented in FIG. 6, is easily carried out by cobalt diacetate in a $CHCl_3/CH_3OH$ mixture at reflux.

b)—Direct synthesis of the complex by the template effect

Figure 7:
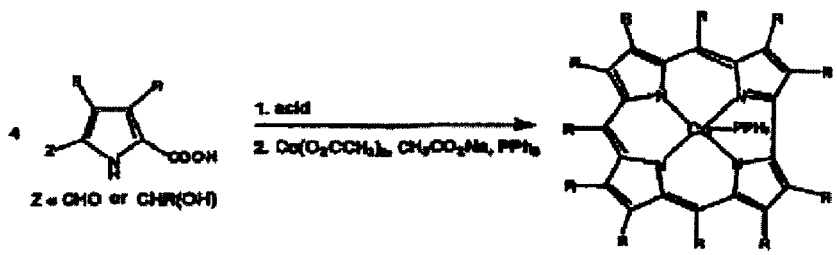
FIG. 7 illustrates the direct synthesis of corrole macrocycle by the template effect.

Another access route, represented in FIG. 7, uses the template effect of the cobalt ion[7-9] to directly obtain the cobalt complex. However, this methodology presupposes access to a complex, the central element of which carries an axial phosphine ligand which may partially inhibit the subsequent coordination of the carbon monoxide.

3. —Co(III) Corroles: Adsorption Properties With Regard to Gases a)—Choice of the Complexes The three cobalt complexes chosen as examples for studying the properties of carbon monoxide and oxygen are represented in FIG. 8. The affinity of Co(III) for carbon monoxide will depend on the electron density present on the Lewis acid metal. The more depleted the metal ion in electrons (by the presence of electron-withdrawing substituents on the corrole), the greater should be its affinity with regard to carbon monoxide. Consequently, corrole III should therefore be expected to have a greater affinity for CO in comparison with corroles I and II (FIG. 9). This scale of reactivity for corroles I, II and III will be confirmed, first, by the measurement of the half-saturation pressure $P_{1/2}(CO)$ and, secondly, by that of the frequency of infrared vibration of the CO bond.

b)—Adsorption of Carbon Monoxide

Adsorption of CO by the various complexes was measured at 21° C. on an ASAP 2010 Micromeritics™ device. The experimental data obtained were processed by a nonlinear adjustment according to a law of Langmuir type:

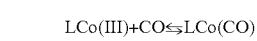

$$V=(V_m \times K \times P)/(1+KP)$$

in which formula $V_m$ is the maximum volume of gas coordinated to the Co(III), K is the stability constant corresponding to the equilibrium:

$$LCo(III)+CO \leftrightarrows LCo(CO)$$

and P is the gas partial pressure.

In all cases, two Langmuir isotherms are necessary to account for the adsorption phenomenon which has to be caused by the cobalt sites having different accessibility in the solid state, as is represented in FIG. 10. In this figure, it is noticed that, even if the cobalt sites are identical from a chemical viewpoint, they are not identical from a "geographical" viewpoint, that is to say that the active sites do not all have the same accessibility for carbon monoxide. This is because, by route 2, carbon monoxide has first to diffuse into the solid before being able to be chemisorbed. In order to account for this phenomenon, it has therefore been necessary to make use of two $P_{1/2}(CO)$ values, i.e. two Langmuir isotherms.

(i)—Corrole I

The complex I does not fix carbon monoxide in the solid state. This result is particularly important since it demonstrates that the adsorption of carbon monoxide cannot be attributed solely to a Co(III) entity. This observation is in agreement with the literature results, for which no coordination of carbon monoxide had been demonstrated with a Co(III) complex. In the present case, the complex I does not possess a sufficient Lewis acidity to make possible the creation of a Co(III)-CO bond.

(ii)—Corrole II

Figure 11:
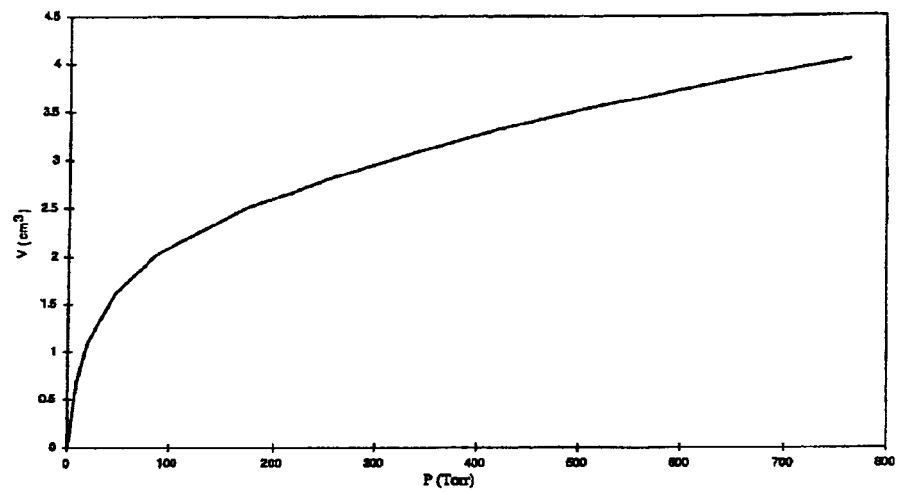
FIG. 11 is a graph illustrating a Langmuir isotherm for the adsorption of carbon monoxide by Corrole II complex.
Figure 12:
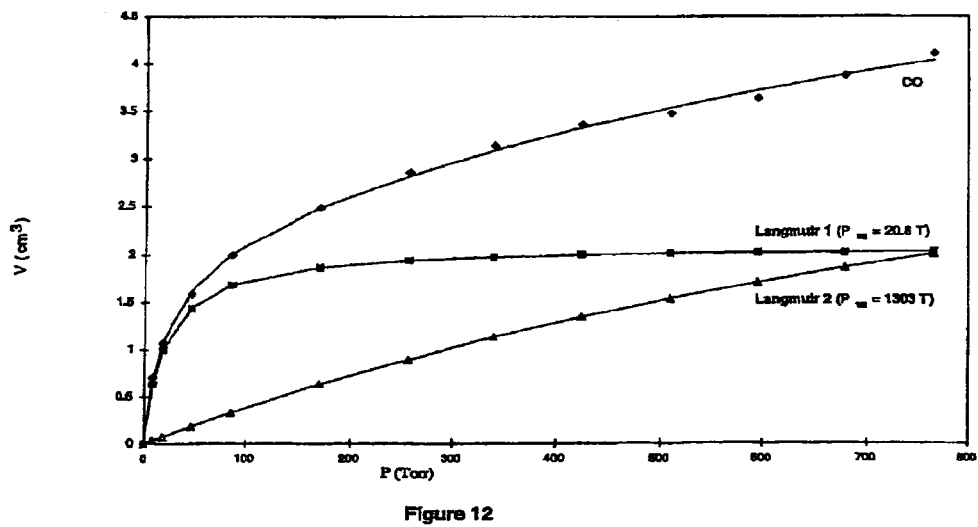
FIG. 12 is a graph illustrating the adsorption isotherm of carbon monoxide by Corrole II complex and the adjustment obtained with two Langmuir isotherms and showing a good match between experimental results and calculated values.
Figure 13:
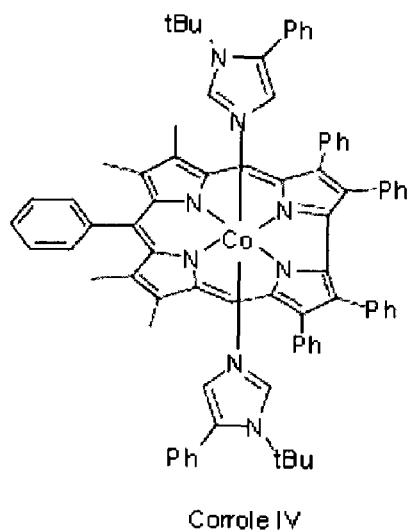
FIG. 13 illustrates the molecular structure of Corrole IV complex.
Figure 14:
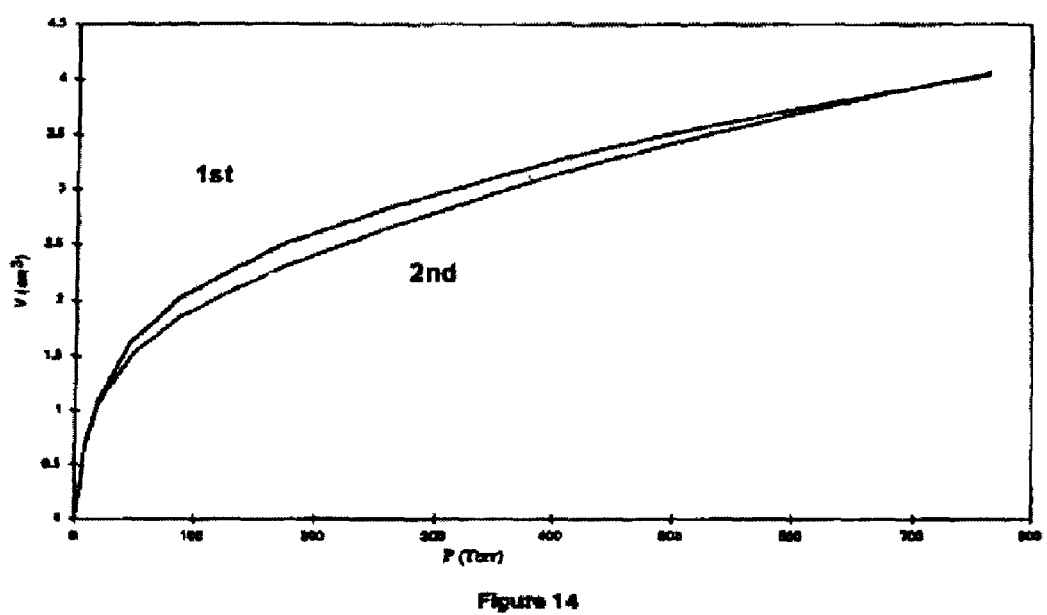
FIG. 14 is a graph illustrating a complete reversibility of the adsorption/desorption of carbon monoxide by Corrole II complex.
Figure 15:
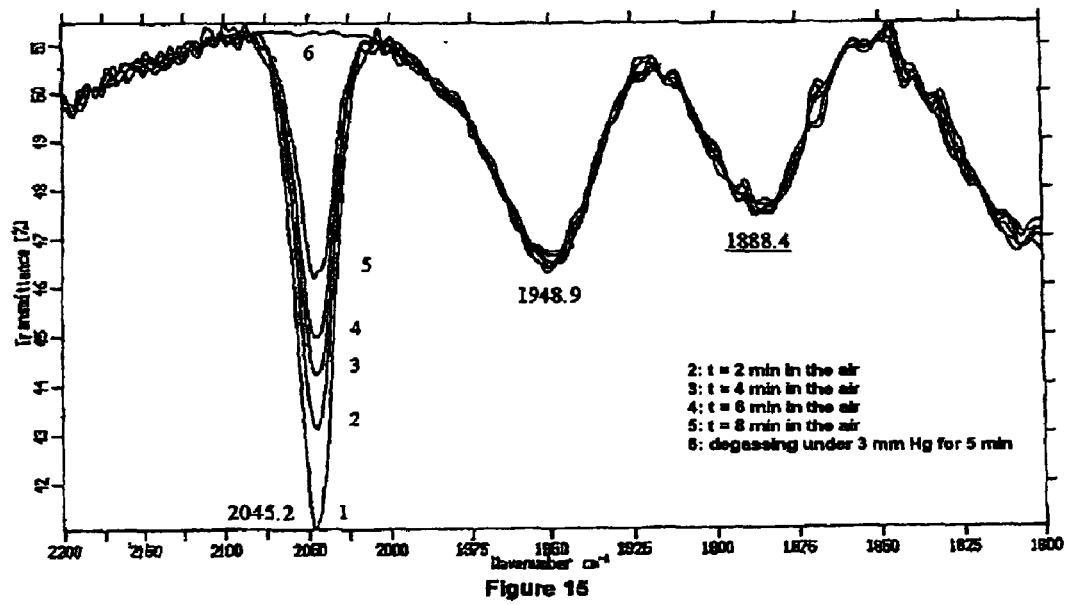
FIG. 15 is a graph illustrating infrared analysis in diffuse reflection mode confirming the complete reversibility of carbon monoxide by Corrole II complex.

The isotherm for adsorption of carbon monoxide by the complex II is represented in FIG. 11. The total volume of carbon monoxide at one atmosphere is 4.11 $cm^3.g^{-1}$, i.e. a yield of 10% with respect to the number of potential sites of the molecule. This result is in agreement with poor accessibility of the Co(III) sites within the solid compound. A dispersion of corrole in a film of Langmuir-Blodgett type or the immobilization of the complex on a solid support of silica or organic polymer type, for example, should render the sites more accessible. However, for an application of sensor type, whatever the volume of CO adsorbed, the detection limits of the sensor will be determined by the CO partial pressure from which the chemosorption of the gas on the corrole occurs. Corrole II fixes CO from low gas pressures. The thermodynamic constants were determined by the nonlinear least squares adjustment method with two Langmuir isotherms (FIG. 12). A very good match between the experimental values and the calculated isotherm is obtained from two Langmuir isotherms. This results in a $P_{1/2}(CO)$ of 20.6 Torr for the first Langmuir isotherm, indicating good affinity of the complex II for CO. This isotherm reflects the chemosorption of CO on readily accessible Co(III) sites, whereas the second Langmuir isotherm accounts both for the diffusion and for the adsorption of the gas on the sites accessible with difficulty. This is why the $P_{1/2}(CO)$ for the second isotherm is very high in this case: 1 303 Torr. Subsequently, only the $P_{1/2}(CO)$ relating to the first Langmuir isotherm will be taken into account. It is important to note that the adsorption of CO indeed corresponds to a phenomenon of chemosorption at the cobalt atom. For this, the properties of adsorption of CO on corrole IV, represented in FIG. 13, the potential sites of which for fixing the gas are blocked by two imidazole molecules, were studied. Corrole IV does not fix carbon monoxide, even at CO pressures of 850 Torr. The infrared spectrum of this compound does not exhibit vibration bands characteristic of CO fixed to a metal. These two results confirm that CO is indeed bonded to the Co(III) in corrole II. For the purpose of an application as carbon monoxide sensor, it is necessary for the process of fixing the gas to be reversible. After degassing the compound II/CO under $10^{-3}$ Torr for 12 h, a second isotherm was recorded. This isotherm and that corresponding to the first adsorption are represented in FIG. 14. This figure demonstrates the complete reversibility of the system with regard to CO, since the volume of CO adsorbed after the second cycle is identical to that measured after the first cycle. This complete reversibility is confirmed by the infrared analysis in diffuse reflection mode of the compound II/CO (FIG. 15). The infrared analysis confirms the good reversibility of the system. This is because, in FIG. 15, a gradual desorption of the CO is indeed observed when the complex is re-exposed to the air (spectra 1 to 5). This desorption results from the decrease in the CO partial pressure in the system. It subsequently becomes complete when the corrole II is degassed under 3 Torr over 5 min, since no band is present at 2 045 $cm^{-1}$ in the infrared (spectrum 6).

(iii)—Corrole III

Figure 16:
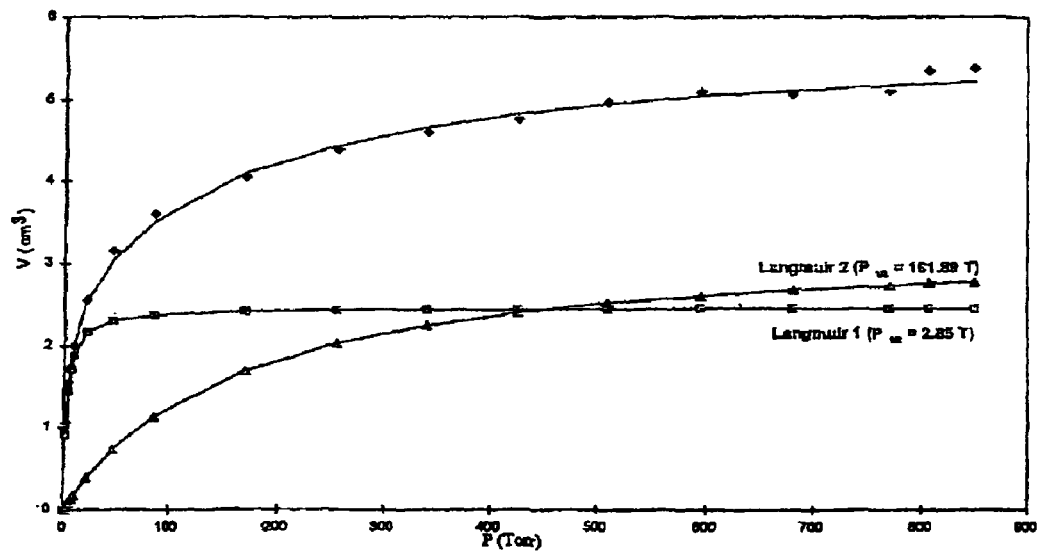
FIG. 16 is a graph illustrating the adsorption isotherm of carbon monoxide by Corrole II complex and the adjustment obtained with two Langmuir isotherms.
Figure 17:
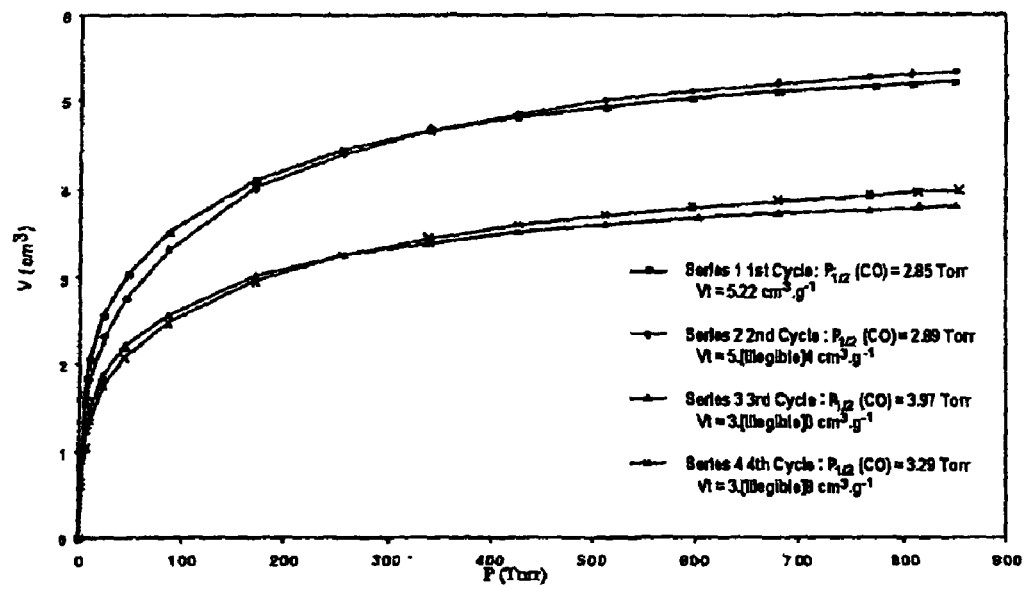
FIG. 17 is a graph illustrating a partial reversibility of the adsorption/desorption of carbon monoxide by Corrole III complex.

FIG. 16 represents the isotherm for adsorption of carbon monoxide for corrole III, and the adjustment obtained with two Langmuir isotherms. As for the preceding compounds, a very good match is observed between the experimental values and the adjustment obtained from two Langmuir isotherms. The first value of $P_{1/2}(CO)$ is 2.85 Torr, which indicates an excellent affinity of the complex III for CO. If this result is compared with that obtained for corrole II ($P_{1/2}(CO)$=20.6 Torr), an increased affinity of corrole III for CO is observed in comparison with corrole II. This confirms the hypothesis of a greater affinity with regard to CO for the complexes in which the Co(III) atom is depleted in electrons (see FIG. 9). The affinity for carbon monoxide can therefore be adjusted as desired by addition of more electron-withdrawing or less electron-withdrawing substituents at the periphery of the corrole macrocycle. The reversibility of the CO adsorption was also tested over four adsorption-desorption cycles for corrole III. The corresponding isotherms are presented in FIG. 17. A partial reversibility is observed during the adsorption-desorption cycles. The total volume of CO adsorbed at 850 Torr is 5.22-5.34 $cm^3.g^{-1}$ for the first two cycles and falls to 3.80-3.98 $cm^3.g^{-1}$ for the third and fourth cycles. This result can be explained in that perhaps not all the sites were freed between the second and third cycles, given the high affinity of corrole III for carbon monoxide. However, it should be pointed out that the value of $P_{1/2}(CO)$ does not vary much according to the cycles. This partial reversibility is confirmed by the infrared analysis in diffuse reflection mode of the compound III/CO. Even after degassing under 3 Torr for 5 min, the band at 2 078.8 $cm^{-1}$ (relating to the CO vibration) has not completely disappeared. This clearly demonstrates the strength of the Co(III)-CO bond in the case of corrole III/CO.

4. $CO/_2$ and $CO/N_2$ Selectivity

Figure 18:
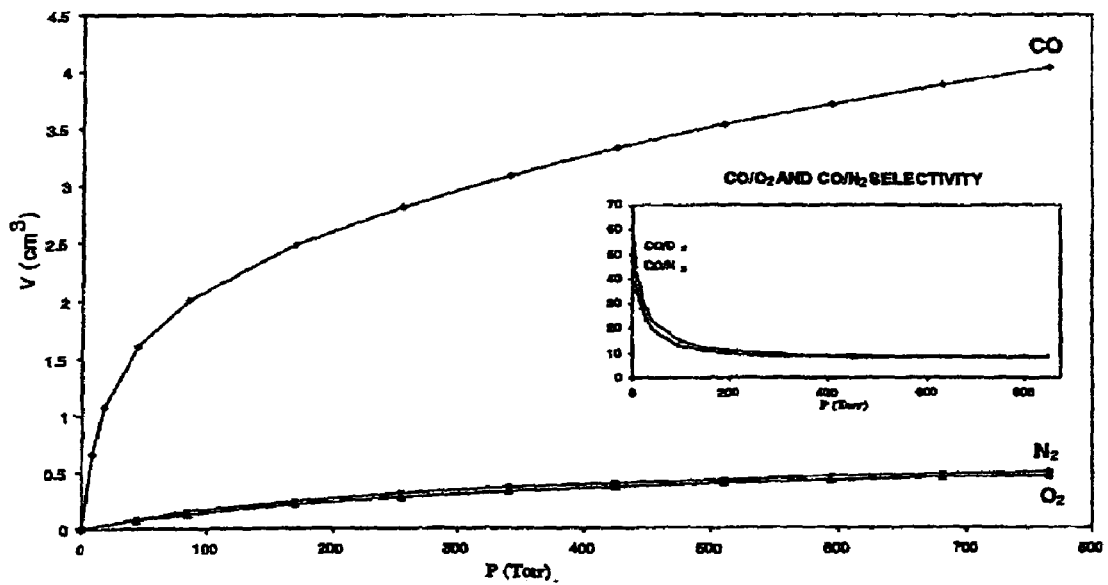
FIG. 18 is a graph illustrating adsorption isotherms for carbon monoxide, carbon dioxide and nitrogen by Corrole II complex.

Many molecules are known for their properties of fixing carbon monoxide but, in all cases, they also fix oxygen. This absence of selectivity (necessary for their use as sensor) makes it impossible to use them for a process for detecting CO in an ambient atmosphere. Furthermore, cobalt or iron complexes, known for their ability to coordinate $O_2$ or CO, prove to be unstable in air over time because of the presence of oxygen and of moisture. Their application as sensor is therefore impossible. The CO, $O_2$ and $N_2$ adsorption isotherms for corrole II are presented in FIG. 18. They reveal the following points:

1—The amount of $N_2$ or $O_2$ fixed is very low with respect to the volume of CO adsorbed, in particular at low pressures.

2—The nitrogen and oxygen adsorption isotherms are identical; this indicates that the phenomenon involved corresponds to physisorption.

Figure 19:
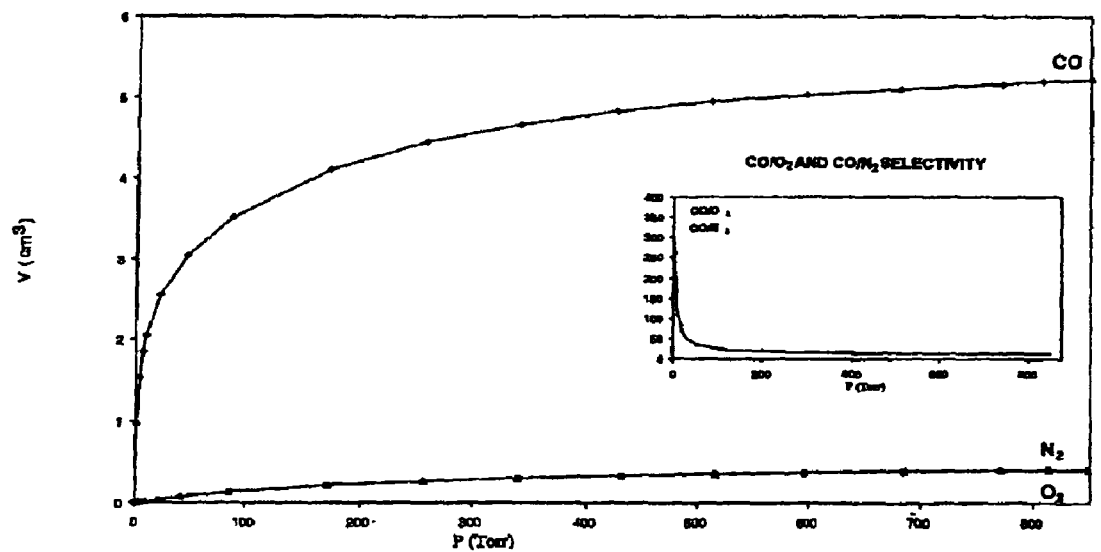
FIG. 19 is a graph illustrating adsorption isotherms for carbon monoxide, carbon dioxide and nitrogen.

From a chemical viewpoint, the $CO/O_2$ or $CO/N_2$ selectivity of the complex is therefore infinite. However, if this selectivity is regarded as being the ratio between the volumes of the various gases adsorbed at a given pressure, it is of the order of 50 for pressures below 5 Torr (insert in FIG. 18). This $CO/O_2$ or $CO/N_2$ selectivity is markedly greater in the case of corrole III, since the amount of CO adsorbed is greater from low pressures. FIG. 19 represents the CO, $O_2$ and $N_2$ adsorption isotherms for corrole III, and the two selectivity curves. The selectivity of the compound is noteworthy at low pressures, since it is of the order of 300 for pressures below 5 Torr, i.e. six times that of corrole II. This results simply from the greater affinity of corrole III for CO. The ratio of the $P_{1/2}(CO)$ values for the two complexes reveals a factor of 7 in favor of corrole III.

Such a $CO/O_2$ selectivity in the solid state is without precedent in the literature and brings to prominence the advantage of such molecules in the field of sensors. These results are compared with those obtained for an iron(II) porphyrin of picket fence type known for more than 20 years for coordinating, in organic solution, $O_2$ and CO with a very high selectivity with regard to CO.[1,10]

5. Picket-fence Fe(II): Adsorption Properties With Regard to Gases

We presented, in FIG. 1, the structure of the picket-fence iron(II) porphyrin ((To-PivPP)Fe(1,2-$Me_2$Im)) with a base of imidazole type coordinated to the iron atom. CO or $O_2$ coordinates to the vacant site of the iron(II) in the porphyrin cavity[11]. This porphyrin complex is in fact currently one of the best synthetic models for myoglobin and hemoglobin since it reversibly coordinates oxygen[1,10,12,13]. This coordination involves an electron transfer from the metal to the oxygen, thereby generating a superoxide anion and bringing about the formal oxidation of iron(II) to iron(III). Thus, the metal centers capable of fixing an oxygen molecule have to have a vacant coordination site and a low degree of oxidation. The formation of the oxygenated entity is stabilized, on the one hand, by the presence of a distal cavity (coordination site opposite to the base) and, on the other hand, by the existence of hydrogen bonds within the cavity between the amide groups of the pivaloyl pickets and the superoxide anion. By modifying these two parameters, it is possible to greatly vary the selectivity of these complexes with regard to oxygen and carbon monoxide. As has been indicated, this molecule is one of the compounds having the greatest affinity in solution for CO. It also fixes oxygen in solution but less strongly. The values of the thermodynamic constants relating to the fixing of CO and $O_2$ by this complex are listed in Table 1 below.

TABLE 1

Stability constant of (To-PivPP)Fe(1,2-Me₂Im) for O₂ and CO.

| | $P_{1/2}O_2$ (Torr) | $P_{1/2}CO$ (Torr) | M = $P_{1/2}O_2/P_{1/2}CO$ | Conditions |
|---|---|---|---|---|
| (To-PivPP)Fe(1,2-Me₂Im) | 38 | 8.9 × 10³ | 4 280 | Toluene, 25° C. |

The ratio M, representative of the $CO/O_2$ selectivity, is one of the highest to date. However, these values were obtained in solution and have never been recorded in the solid state for carbon monoxide, and just one publication describes the coordination of oxygen[14] to picket-fence iron(II) in a solid state. It was therefore important to carry out a full study in the solid state by making series of measurements analogous to those carried out on the corroles.

(i)—Adsorption of CO

Figure 20:
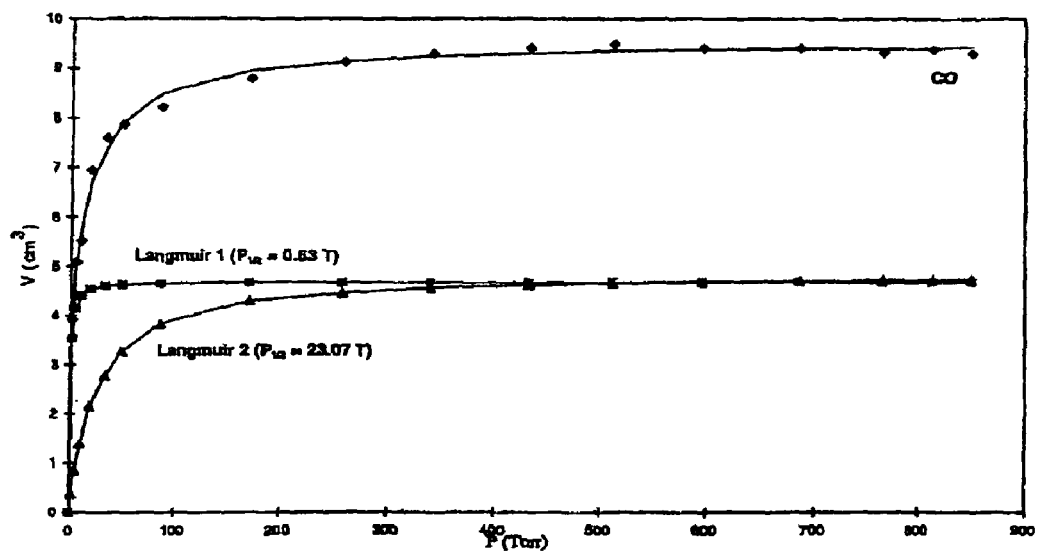
FIG. 20 is a graph illustrating the adsorption isotherm of carbon monoxide by solid state (To-PivPP) Fe (1,2 Me$_2$ Im) complex and the adjustment obtained with two Langmuir isotherms; and showing the very good match between experimental results and calculated values.
Figure 21:
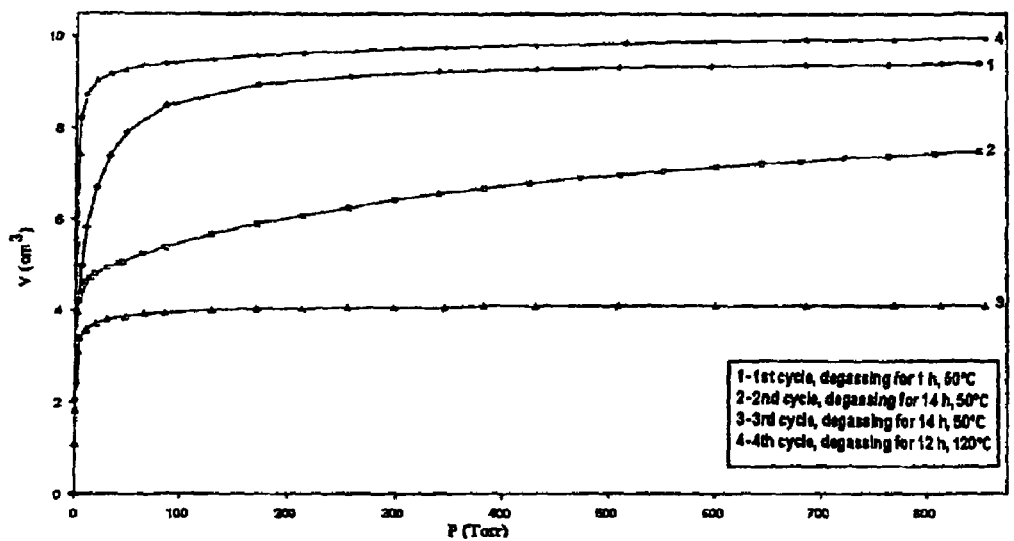
FIG. 21 is a graph illustrating the incomplete reversibility of the adsorption/desorption of carbon monoxide by solid state (To-PivPP) Fe (1,2 Me$_2$ Im) complex.
Figure 22:
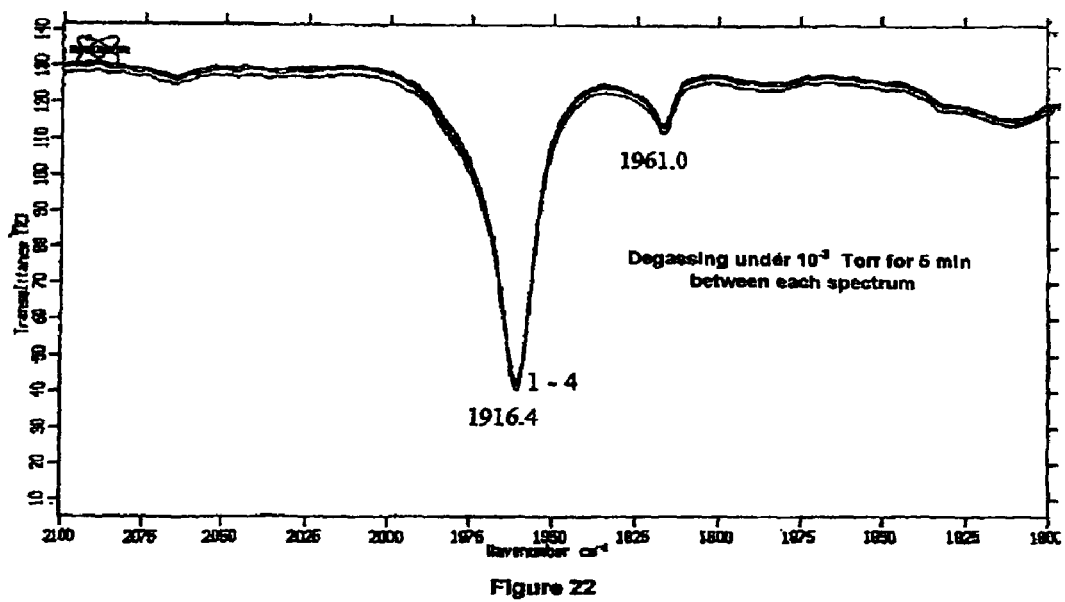
FIG. 22 is a graph illustrating the infrared analysis in diffuse reflection mode confirming the great stability of the Fe—CO bond.

FIG. 20 represents the isotherm for adsorption of carbon monoxide in the solid state for (To-PivPP)Fe(1,2-Me₂Im), and the adjustment obtained with two Langmuir isotherms. A $P_{1/2}(CO)$ value of 0.63 Torr was calculated for the first Langmuir isotherm, indicating an excellent affinity of (To-PivPP)Fe(1,2-Me₂Im) for CO. As in the case of the corrole complexes, the second Langmuir isotherm accounts both for the diffusion and for the adsorption of the gas on less accessible sites. However, the $P_{1/2}(CO)$ is relatively low: 23 Torr. This reflects a good affinity of these "less accessible" sites for CO. The total volume adsorbed at P=850 Torr is 9.29 cm³.g⁻¹, which represents 50% of the active sites. The reversibility of (To-PivPP)Fe(1,2-Me₂Im) with regard to CO was also studied (see FIG. 21). Under relatively mild degassing conditions (50° C.), the fixing of CO to (To-PivPP)Fe(1,2-Me₂Im) is not completely reversible (cycles 1-3, FIG. 21). This is explained by a very strong bond existing between the iron and the CO. On the other hand, after degassing at 120° C. for 12 h, the total volume adsorbed is slightly greater than that obtained during the first cycle (isotherms 1 and 4). It should also be noted that, for the four cycles, the value of $P_{1/2}(CO)$ is between 0.3 and 0.6 Torr. The great stability of the Fe—CO bond is confirmed by the infrared analysis in diffuse reflection mode of (To-PivPP) Fe(1,2-Me₂Im)/CO (FIG. 22). For compounds possessing an Fe—CO bond, the band corresponding to the vibration of the CO bond appears at a low frequency, which indicates that the Fe—CO bond is strong, because of a very marked π retrodonation from the metal to the ligand.

(ii)—Adsorption of $O_2$

Figure 23:
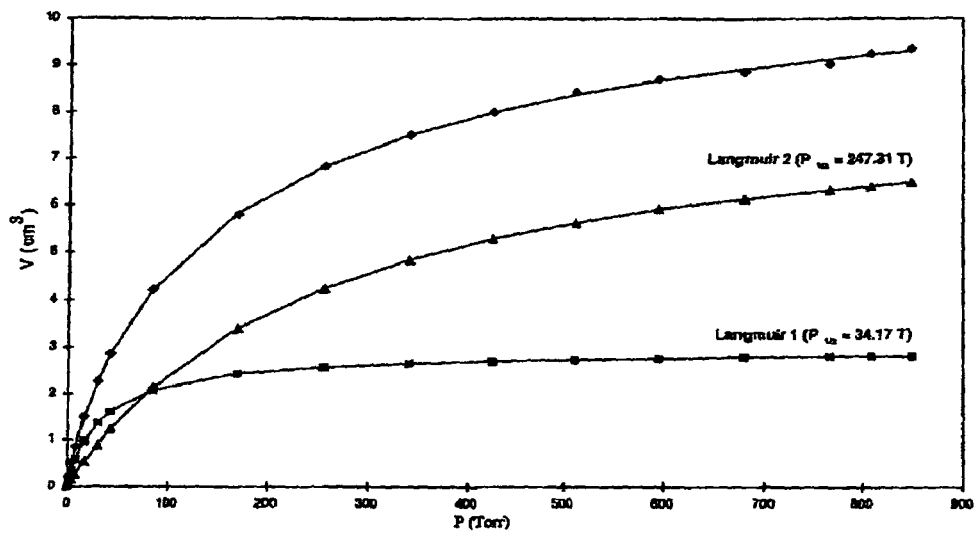
FIG. 23 is a graph illustrating the adsorption isotherm of oxygen by solid state (To-PivPP) Fe (1,2 Me$_2$ Im) complex and the adjustment obtained with two Langmuir isotherms and showing the good match between experimental results and calculated values.
Figure 24:
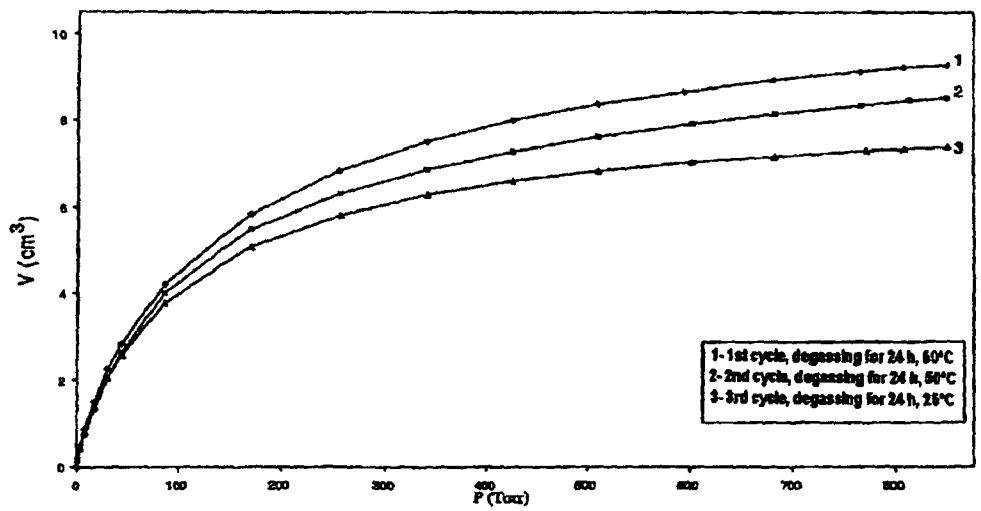
FIG. 24 is a graph illustrating the reversibility of the adsorption/desorption of oxygen by solid state (To-PivPP) Fe (1,2-Me$_2$ Im) complex showing better reversibility than that for carbon monoxide.

FIG. 23 represents the isotherm for adsorption of oxygen in the solid state for (To-PivPP)Fe(1,2-Me₂Im), and the adjustment obtained with two Langmuir isotherms. A $P_{1/2}(O_2)$ value of 34.2 Torr was calculated for the first Langmuir isotherm, indicating a good affinity of the compound for $O_2$. This affinity is markedly lower than for CO ($P_{1/2}(CO)=0.63$ Torr; FIG. 23). A behavior in agreement with that obtained in solution is clearly re-encountered here. The total volume adsorbed at P=850 Torr is 9.29 cm³.g⁻¹ (result identical to that obtained for CO), which represents 50% of the active sites. Likewise, the reversibility of (To-PivPP)Fe(1,2-Me₂Im) with regard to $O_2$ was studied (see FIG. 24). In contrast to what was observed for carbon monoxide, the reversibility appears to be better for oxygen, since the total volume adsorbed does not decrease very much between each cycle. This is explained by a weaker bond between $O_2$ and the iron; mild degassing conditions are then sufficient to desorb $O_2$. Complete reversibility should be obtained by heating under vacuum.

6. Comparison Between the Corroles (Co(III)) and the Picket Fence (Fe(II))

The values obtained for the cobalt(III) corroles and for (To-PivPP)Fe(1,2-Me₂Im) are presented in Table 2.

TABLE 2

Comparison between the cobalt corroles and (To-PivPP)Fe(1,2-Me₂Im).

| Compounds | $P_{1/2}O_2$ (Torr) | $P_{1/2}CO$ (Torr) | M = ($P_{1/2}O_2/P_{1/2}CO$) | Reversibility |
|---|---|---|---|---|
| (To-PivPP)Fe(1,2-Me₂Im) | 34.17 | 0.63 | 54 | A |
| Corrole II | 391.35 | 20.6 | 19 | B |
| Corrole III | 263.78 | 2.85 | 93 | C |

(A: partial at 20° C., complete at 120° C.; B: complete at 20° C.; C: partial at 20° C.)

It is important to remember that the oxygen adsorbed by the corroles corresponds to a physisorption phenomenon. Conversely, for (To-PivPP)Fe(1,2-Me₂Im), a chemical bond between the iron and $O_2$ is involved. The "chemical" selectivity is therefore infinite for corroles II and III. However, even taking into account physisorbed $O_2$, corrole III exhibits a markedly greater selectivity than that obtained for the porphyrin. Furthermore, it can be handled in the air and does not decompose in the presence of moisture. These results, which are without precedent, demonstrate the potentialities of such a molecule in various fields of application and in particular in that of carbon monoxide sensors.

7. Experimental Part (i)—Synthesis of Corrole I

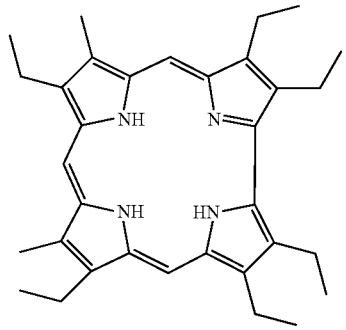

15 ml of 33% hydrobromic acid in acetic acid are added to a suspension of 2.38 g (7.5 mmol) of 5,5'-dicarboxy-3,3'-diethyl-4,4'-dimethyldipyrrylmethane and of 2.26 g (15 mmol) of 3,4-diethyl-2-formylpyrrole [or 2.15 g (7.5 mmol) of 3,3'-diethyl-5,5'-diformyl-4,4'-dimethyldipyrrylmethane and 2.51 g (15 mmol) of 2-carboxy-3,4-diethylpyrrole] in 120 ml of ethanol at reflux. The reaction mixture is then brought to reflux for 10 minutes. After cooling the solution, the biladiene-a,c (reaction intermediate) precipitates during the addition of 150 ml of diethyl ether. The biladiene-a,c is filtered off, rinsed with ether and dried. A purple powder is obtained with a yield of 70%. The biladiene-a,c is subsequently dissolved in 500 ml of methanol saturated with $NaHCO_3$ and the solution is stirred for 10 minutes. 730 mg of p-chloranil are subsequently added and, after stirring for an additional 10 minutes, 7 ml of 50% hydrazine hydrate in water are added. After stirring for 10 minutes, the corrole precipitates in the form of a purple-pink powder. The corrole is then filtered off and washed copiously with water. The corrole is subsequently recrystallized from a CH$_2$Cl$_2$/CH$_3$OH mixture, filtered off and dried.

Corrole I is obtained with a yield of 65%.

Proton NMR (CDCl$_3$) (δ in ppm): −2.93 (s, 3H, NH); 1.84 (t, 6H, CH$_3$); 1.87 (t, 6H, CH$_3$); 1.89 (t, 6H, CH$_3$); 3.38 (s, 6H, CH$_3$); 3.90 (q, 4H, CH$_2$); 3.95 (q, 4H, CH$_2$); 4.06 (q, 4H, CH$_2$); 9.51 (s, 1H, H-10); 9.53 (s, 2H, H-5, 15).

Infrared spectrometry (KBr; v in cm$^{-1}$): 3350 (NH); 2961 (CH); 2928 (CH); 2867 (CH).

Mass spectrometry (EI): m/z=494 (M$^{+\bullet}$) (100)

Percentage analysis for C$_{33}$H$_{42}$N$_4$:

calculated: C 80.1%; H 8.6%; N 11.3% found: C 79.7%; H 8.6%; N 11.4%

UV-Visible spectrophotometry (CH$_2$Cl$_2$): λ$_{max}$, nm (ε×10$^{-3}$ M$^{-1}$.cm$^{-1}$): 395 (126.5); 407 (101.2); 549 (18.9); 593 (23.6).

(ii)—Synthesis of Corrole II

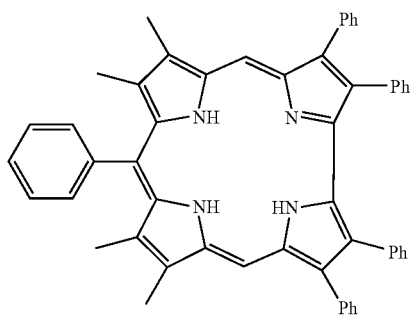

After dissolution of 4.72 g (12.8 mmol) of 5,5'-dicarboxy-3,3',4,4'-tetramethyldipyrryltoluene in 200 ml of trifluoroacetic acid, the red solution is stirred at ambient temperature for 5 minutes. A solution of 7 g (25.6 mmol) of 3,4-diphenyl-2-formyl-pyrrole in 200 ml of methanol is then added dropwise. Stirring is maintained for 15 minutes and 70 ml of 33% hydrobromic acid in acetic acid are added. The reaction mixture is stirred for 15 minutes and then the solvents are evaporated. A solid is obtained which has green highlights (biladiene-a,c). The biladiene-a,c is then dissolved in 1 l of methanol saturated with NaHCO$_3$ and is stirred for 15 minutes. 4.3 g of p-chloranil are then added and the reaction medium is again stirred for 15 minutes. Finally, 43 ml of 50% hydrazine hydrate in water are added and, after stirring for an additional 15 minutes, the solvents are evaporated. The solid obtained is taken up in dichloromethane and washed with water to neutral pH. The organic phase is subsequently dried over MgSO$_4$, filtered and evaporated. The solid obtained is passed through an alumina chromatographic column (eluent: 100% CH$_2$Cl$_2$). The purple fraction which elutes in the solvent front is collected and evaporated. The corrole is subsequently recrystallized from a CH$_2$Cl$_2$/CH$_3$OH mixture, filtered off and dried.

Corrole II is obtained with a yield of 10%.

Proton NMR (CDCl$_3$) (δ in ppm): 2.22 (s, 6H, CH$_3$); 3.17 (s, 6H, CH$_3$); 6.57-7.95 (m, 25H, Ar—H); 9.40 (s, 2H, H-5, 15).

Mass spectrometry (LSIMS): m/z=734 (M$^{+\bullet}$) (100).

UV-Visible spectrophotometry (CH$_2$Cl$_2$): 4$_{max}$, nm (ε×10$^{-3}$ M$^{-1}$.cm$^{-1}$): 418 (85.3); 566 (14.3); 604 (12.1).

(iii)—Synthesis of Corrole III

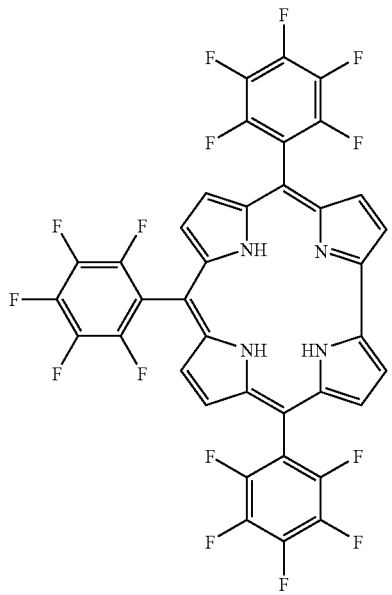

The synthesis described here was developed by the team of Professor Gross in 1999[5]. This synthesis makes it possible to obtain, in a single stage, a corrole from two commercial products at a lower cost. The synthesis is performed in the presence of a solid support of alumina type and is carried out without solvent. 2.94 g (15 mmol) of pentafluorobenzaldehyde and 0.967 ml (15 mmol) of pyrrole are added to 200 mg of alumina which is dehydrated and milled beforehand. The reaction mixture is stirred at 60° C. for 4 hours. The solid obtained is then dissolved in dichloromethane and 200 mg of DDQ are added. The purple solution is evaporated and the solid obtained is passed through an alumina chromatographic column (eluent: 100% CH$_2$Cl$_2$). The purple fraction which migrates in the solvent front is collected and then evaporated. The corrole is subsequently recrystallized from a CH$_2$Cl$_2$/CH$_3$OH mixture, filtered off and dried.

Corrole III is obtained with a yield of 15%.

Proton NMR (CDCl$_3$) (δ in ppm): 7-9 (4 dd, 8H, Hpyr.).

Mass spectrometry (LSIMS): m/z=796 (M$^{+\bullet}$) (100).

(iv)—Metallation of Corroles I, II and III

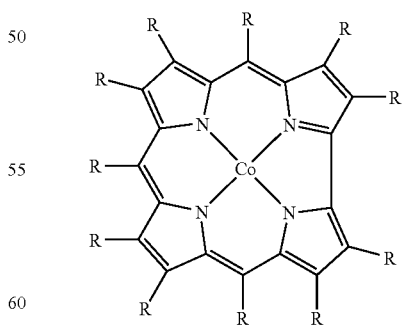

The corrole is dissolved in chloroform and is brought to reflux. 1.2 equivalents of Co(O$_2$CCH$_3$)$_2$, dissolved in the minimum amount of methanol, are added to this solution. The reaction medium is stirred at reflux for 10 minutes and then the solvents are evaporated. The solid is subsequently taken up in dichloromethane and washed with water. The organic phase is subsequently dried over $MgSO_4$, filtered and then evaporated. The cobalt corrole obtained is recrystallized from a $CH_2Cl_2/CH_3OH$ mixture, filtered off and dried.

The cobalt corroles are obtained with yields of greater than 90%. The main analytical characteristics of the complexes obtained are summarized in the following table:

| (Corrole)Co | UV-Visible λmax ($\epsilon \times 10^{-4}$ $M^{-1} \cdot cm^{-1}$) | MALDI-TOF |
|---|---|---|
| (Corrole I)Co | 381 (7.7); 502 (0.9) | m/z = 550 |
| (Corrole II)Co | 399 (4.7); 531 (1.2) | m/z = 788 |
| (Corrole III)Co | 394 (2.8); 501 (1.0) | m/z = 852 |

(v)—Access to Organic-Inorganic Hybrid Materials
a) Grafting to Silica

The grafting to silica is carried out by anchoring the corrole macrocycle, which may or may not be metallated, via a functionalized arm to the free silanol functional groups of silica gel according to the following reaction process:

The first stage consists of the addition of the functionalized arm to just one of the aryl groups $R_a$, $R_b$ or $R_c$ of the corrole (Scheme 1). This arm can be functionalized by vinyl or amino groups or by a halogen atom. The length of this arm can vary from zero carbon atoms (the functional group is then directly attached to the trialkoxysilane unit) to a maximum of four atoms. The aryl residue to which the spacer arm will be attached is functionalized in the $R_9$, $R_{10}$, $R_{12}$ or $R_{13}$ position by the appropriate group according to Scheme 1.

The second stage corresponds to the grafting of the functionalized macrocycle to the silica gel by reaction of the trialkoxysilyl unit with one, two or three accessible silanol functional groups of the silica (Scheme 2).

b) Direct Formation of the Material by the Sol-Gel Technique

The sol-gel materials are synthesized by proceeding in the following way:

Route 1: Polycondensation of corroles or metallocorroles mono-, di- and trisubstituted in the meso position ($R_a$, $R_b$ and $R_c$) by spacers possessing trialkoxysilyl endings (Scheme 3).

The preliminary functionalization of the aryl groups $R_a$, $R_b$ and $R_c$ will be carried out according to the same protocol as that described above for the grafting to the silica gel (Scheme 1). The polycondensation will be carried out by reaction of the trisubstituted corrole or metallocorrole mentioned beforehand with the stoichiometric amount of water in the presence of a catalyst (fluoride, acid or base) in any organic solvent which makes it possible to dissolve the reaction medium.

Route 2: Copolymerization of corroles or metallocorroles mono-, di- and trisubstituted in the meso position ($R_a$, $R_b$ and $R_c$) by arms possessing trialkoxysilyl endings with a tetraalkoxysilane (formation of a cogel) (Scheme 3).

The functionalization of the corrole or metallocorrole is entirely identical to that described above. The copolycondensation will be carried out by reaction of the trisubstituted corrole or metallocorrole mentioned beforehand with the tetraalkoxysilane and the stoichiometric amount of water in the presence of a catalyst (fluoride, acid or base) in any organic solvent which makes it possible to dissolve the reaction medium.

c) Direct Grafting to a Material of MTS Type

This family of materials, discovered by Beck in 1992, is known as MTS (Mesoporous Templated Silica) and two representatives of this family, known as HMS (Hexagonal Mesoporous Silica) or MSU, correspond to our requirements. The arrangement of the HMS or MSU material is brought about by polycondensation of a hydrolyzable precursor in the presence of a neutral surface-active agent, such as a $C_8$ to $C_{18}$ primary amine (HMS) or a polyethylene oxide (MSU). The structuring agent is easily removed by extraction with ethanol. The removal of the surfactant thus releases hexagonal channels having a uniform mean diameter and exhibiting a noteworthy accessibility to various molecules. The anchoring of the corrole unit within the pores of the material can be carried out by reaction of the macrocycle, mono- or difunctionalized by a sequence comprising an end trialkoxysilane group, with the free silanol groups of the material (Scheme 4).

The preliminary functionalization of the aryl groups $R_a$ and/or $R_b$ and/or $R_c$ is carried out according to the same protocol as that mentioned above (Scheme 1).

(v) Access to Organic-Inorganic Hybrid Materials
a) Grafting to Silica

Figure 25:
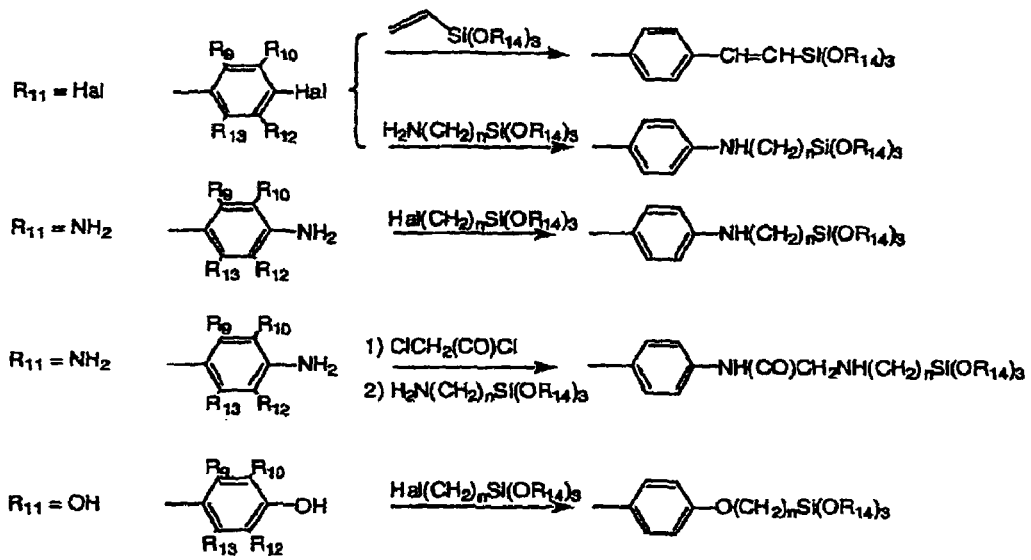
FIG. 25 illustrates the first stage of grafting to silica by the reaction of the functionalized arm to just one of the aryl groups $R_a$, $R_b$ or $R_c$ of the Corrole complex.

The grafting to silica is carried out by anchoring the corrole macrocycle, which mayor may not be metallated, via a functionalized arm to the free silanol functional groups of silica gel according to the following reaction process:

The first stage consists of the addition of the functionalized arm to just one of the aryl groups Ra, $R_b$ or $R_c$ of the corrole (FIG. 25). This arm can be functionalized by vinyl or amino groups or by a halogen atom. The length of this arm can vary from zero carbon atoms (the functional group is then directly attached to the trialkoxysilane unit) to a maximum of four atoms. The aryl residue to which the spacer arm will be attached is functionalized in the $R_9$, $R_{10}$, $R_{12}$ or $R_{13}$ position by the appropriate group according to FIG. 25.

Figure 26:
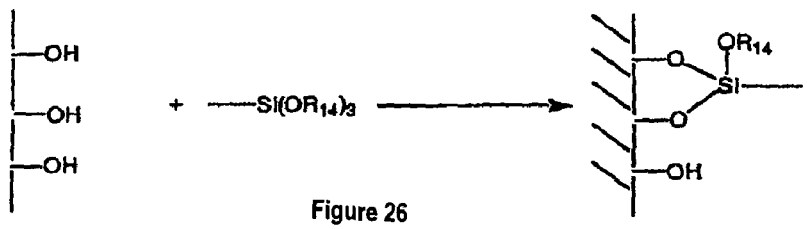
FIG. 26 illustrates the second stage of grafting the functionalized corrole macrocycle to silica gel by the reaction of the trialkoxysilyl unit with one, two or three accessible silanol functional groups of the silica.

The second stage corresponds to the grafting of the functionalized macrocycle to the silica gel by reaction of the trialkoxysilyl unit with one, two or three accessible silanol functional groups of the silica (FIG. 26).

b) Direct Formation of the Material by the Sol-Gel Technique

Figure 27:
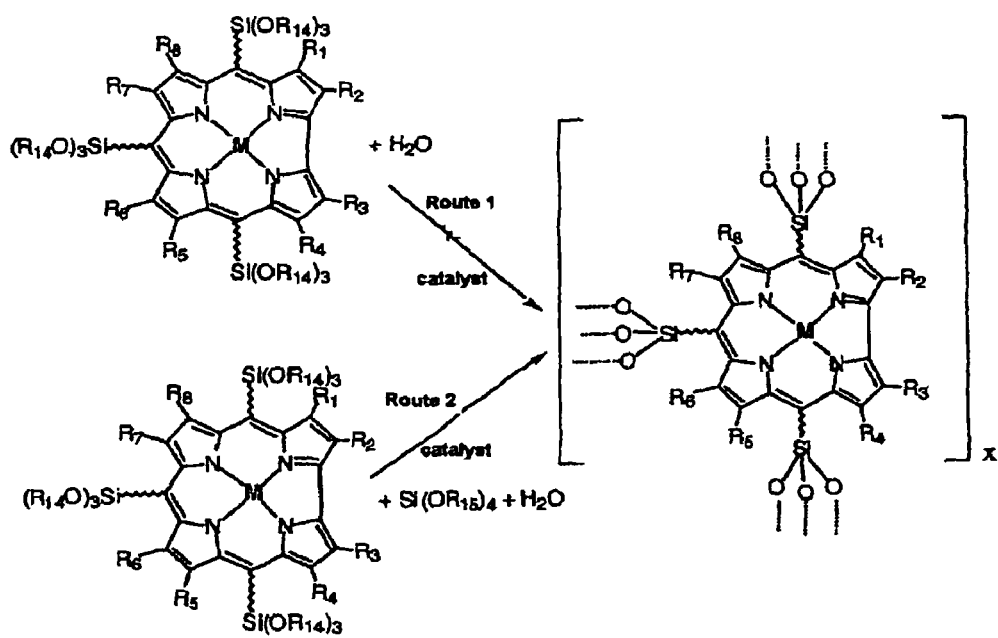
FIG. 27 illustrates the copolymerization of corrole macrocycle complex or metallo-corroles mono-, di-, and trisubstituted in the meso position ($R_a$, $R_b$, and $R_c$) by arms possessing trialkoxysillyl endings with a tetraalkoxysilane.

The sol-gel materials are synthesized by proceeding in the following way:

Route 1: Polycondensation of corroles or metallocorroles, mono-, di- and trisubstituted in the meso position ($R_a$, $R_b$ and $R_c$) by spacers possessing trialkoxysilyl endings (FIG. 27).

The preliminary functionalization of the aryl groups $R_a$, $R_b$ and $R_c$, will be carried out according to the same protocol as that described above for the grafting to the silica gel (FIG. 25). The poly-condensation will be carried out by reaction of the trisubstituted corrole or metallocorrole mentioned beforehand with the stoichiometric amount of water in the presence of a catalyst (fluoride, acid or base) in any organic solvent which makes it possible to dissolve the reaction medium.

Route 2: Copolymerization of corroles or metallocorroles mono-, di- and trisubstituted in the meso position ($R_a$, $R_b$ and $R_c$) by arms possessing trialkoxysilyl endings with a tetraalkoxysilane (formation of a cogel) (FIG. 27).

The functionalization of the corrole or metallocorrole is entirely identical to that described above. The copolycondensation will be carried out by reaction of the trisubstituted corrole or metallocorrole mentioned beforehand with the tetraalkoxysilane and the stoichiometric amount of water in the presence of a catalyst (fluoride, acid or base) in any organic solvent which makes it possible to dissolve the reaction medium.

c) Direct Grafting to a Material of MTS Type

Figure 28:
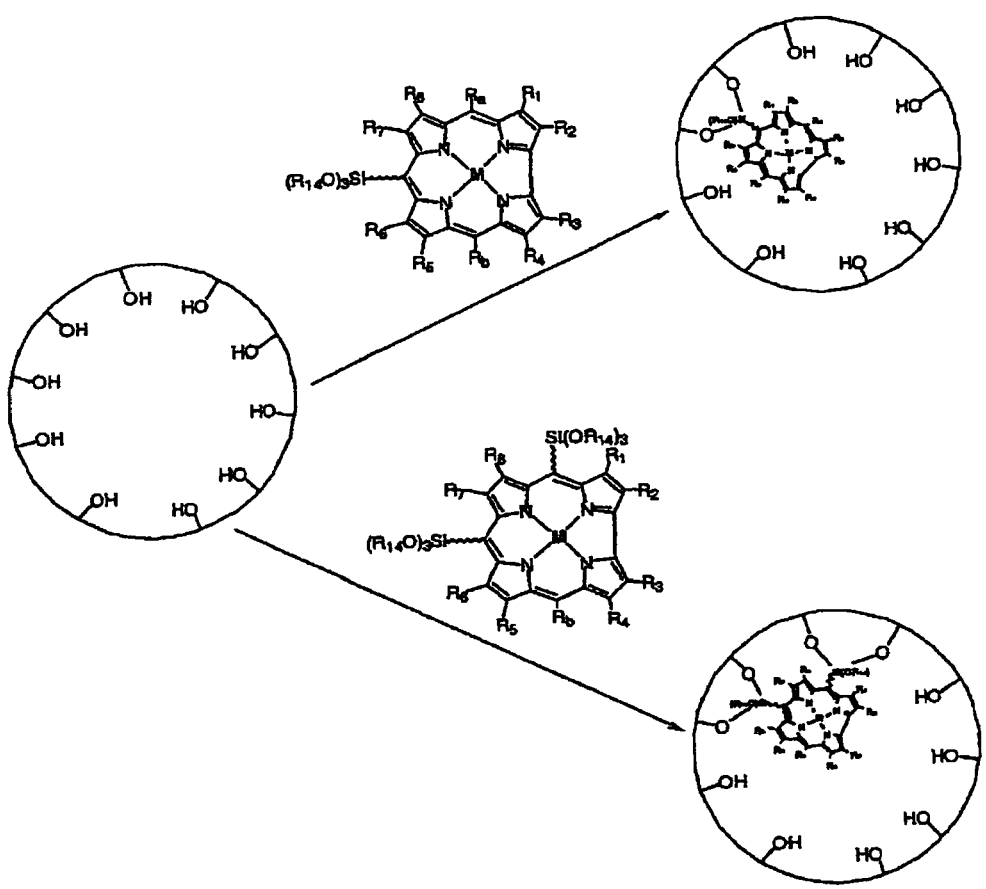
FIG. 28 illustrates the direct anchoring of the correle macrocycle unit within the pores of mesoporous templated silica (MtS) materials.

This family of materials, discovered by Beck in 1992, is known as MTS (Mesoporous Templated Silica) and two representatives of this family, known as HMS (Hexagonal Mesoporous Silica) or MSU, correspond to our requirements. The arrangement of the HMS or MSU material is brought about by polycondensation of a hydrolyzable precursor in the presence of a neutral surface-active agent, such as a $C_8$ to $C_{18}$ primary amine (HMS) or a polyethylene oxide (MSU). The structuring agent is easily removed by extraction with ethanol. The removal of the surfactant thus releases hexagonal channels having a uniform mean diameter and exhibiting a noteworthy accessibility to various molecules. The anchoring of the corrole unit within the pores of the material can be carried out by reaction of the macrocycle, mono- or difunctionalized by a sequence comprising an end trialkoxysilane group, with the free silanol groups of the material (FIG. 28).

The preliminary functionalization of the aryl groups $R_a$ and/or $R_b$ and/or $R_c$ is carried out according to the same protocol as that mentioned above (FIG. 25).

REFERENCES (1) J. P. Collman, L. Fu, *Acc. Chem. Res.*, 1999, 32, 455-463.
(2) R. Paolesse, *Heteroporphyrins, Expanded Porphyrins and Related Macrocycles*, in the *Porphyrin Handbook*, Vol. 2, Smith, K. M.; Kadish, K. M.; Guilard, R., Academic Press, New York, 2000, p. 201-233.
(3) A. W. Johnson, I. T. Kay, *Proc. Chem. Soc.*, 1964, 89-90.
(4) A. W. Johnson, I. T. Kay, *Proc. Roy. Soc. A*, 1965, 288, 334-341.
(5) Z. Gross, N. Galili, L. Simkhovich, I. Saltsman, M. Botoshansky, D. Bläser, R. Boese, I. Goldberg, *Org. Lett.*, 1999, 1, 599-602.
(6) M. J. Broadhurst, R. Grigg, A. W. Johnson, *J. Chem. Soc., Perkin I*, 1972, 1124-1135.
(7) R. Paolesse, S. Licoccia, M. Fanciullo, E. Morgante, T. Boschi, *Inorg. Chim. Acta*, 1993, 203, 107-114.
(8) R. Paolesse, S. Licoccia, G. Bandoli, A. Dolmella, T. Boschi, *Inorg. Chem.*, 1994, 33, 1171-1176.
(9) S. Licoccia, E. Tassoni, R. Paolesse, T. Boschi, *Inorg. Chim. Acta*, 1995, 235, 15-20.
(10) J. P. Collman, J. I. Brauman, B. L. Iverson, J. L. Sessler, R. M. Morris, Q. H. Gibson, *J. Am. Chem. Soc.*, 1983, 105, 3052-3064.
(11) J. P. Collman, R. R. Gagne, C. A. Reed, T. R. Halbert, G. Lang, W. T. Robinson, *J. Am. Chem. Soc.*, 1975, 97, 1427-1439.
(12) J. P. Collman, J. I. Brauman, T. R. Halbert, K. S. Suslick, *Proc. Natl. Acad. Sci. USA*, 1976, 73, 3333-3337.
(13) J. P. Collman, *Inorg. Chem.*, 1997, 36, 5145-5155.
(14) J. P. Collman, J. I. Brauman, K. S. Suslick, *J. Am. Chem. Soc.*, 1975, 97, 7185-7186.

The invention claimed is:

1. A silica gel composition comprising a compound of formula $G(Y)_\alpha$, wherein:
G is an organometallic cation of formula (II'),

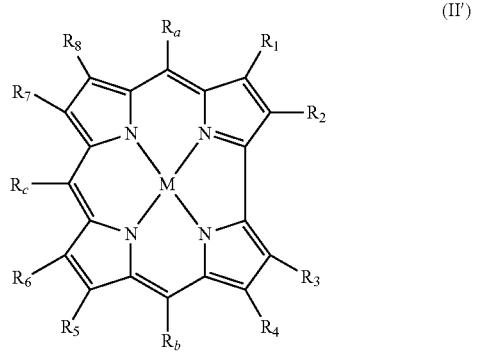

(II')

$R_1$, $R_2$, $R_2$, and $R_4$ are identical or different radicals each independently selected from the group consisting of:
i) hydrogen atoms,
ii) linear or branched alkyl radicals having 1 to 4 carbon atoms,
iii) unsubstituted phenyl radicals, and
iv) substituted phenyl radicals substituted by one or more identical or different radical each independently selected from the group consisting of vinyl, hydroxyl, nitro, amino, cyano, carboxyl, bromo, chloro, fluoro, iodo, benzyloxy, and hydroxymethyl radicals,
linear or branched alkyl radicals having 1 to 4 carbon atoms, said alkyl radicals unsubstituted or substituted by one or more bromo, chloro, fluoro or iodo group, and
linear or branched alkyloxy radicals having 1 to 4 carbon atoms, said alkyloxy radicals unsubstituted or substituted by one or more bromo, chloro, fluoro or iodo group,
$R_5$, $R_6$, $R_7$, and $R_8$, are identical or different radicals each independently selected from the group consisting of:
i) hydrogen atoms, and
ii) linear or branched alkyl radicals having 1 to 4 carbon atoms, and
$R_a$, $R_b$, and $R_c$ are identical or different radicals each independently selected from the group consisting of:
i) hydrogen atoms,
ii) unsubstituted phenyl radicals, and
iii) substituted phenyl radicals substituted by one or more identical or different radical each independently selected from the group consisting of vinyl, hydroxyl, nitro, amino, cyano, carboxyl, bromo, chloro, fluoro, iodo, benzyloxy, and hydroxymethyl radicals,
linear or branched alkyl radicals having 1 to 4 carbon atoms, said alkyl radical being unsubstituted or substituted by one or more bromo, chloro, fluoro or iodo groups, and
linear or branched alkyloxy radicals having 1 to 4 carbon atoms, said alkyloxy radical being unsubstituted or substituted by one or more bromo, chloro, fluoro or iodo group,
and wherein, at least one of $R_a$, $R_b$, and $R_c$ is an unsubstituted phenyl radical or a substituted phenyl radical;
M is at least one metal cation selected from the group consisting of cobalt, rhodium, iridium, manganese, iron, ruthenium, and osmium;
Y is an organic or inorganic anion; and
α is an integer or decimal number such that the compound of formula $G(Y)_\alpha$ is electrically neutral,
wherein the compound of formula $G(Y)_\alpha$ is covalently bonded to a silica gel via spacer arms, and said spacer arms are divalent radicals bonded to a 2-, 3-, or 4-position of said at least one $R_a$, $R_b$, or $R_c$ phenyl radical and to a free silanol functional group (Si—O) of said silica gel.

2. The composition according to claim 1, wherein M is a metal cation selected from the group consisting of Fe(III) and Co(III).

3. The composition according to claim 1, wherein said divalent radical is selected from the group consisting of:

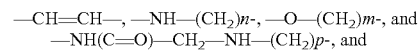

n, m, and p are identical or different integers independently in a range of 0 to 4.

4. The composition according to claim 1, wherein,
$R_a$, $R_b$, and $R_c$ are unsubstituted or substituted phenyl radicals,
said substituted phenyl radical being substituted at the 2-, 3-, or 4-position by a monovalent radical having an end group comprising —Si(OR$_{14}$)$_3$, and
$R_{14}$ a radical selected from the group consisting of methyl, ethyl, and isopropyl radicals.

5. The composition according to claim 4, wherein said monovalent radical is selected from the group consisting of:

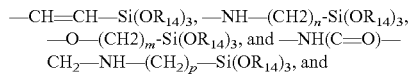

n, m, and p are identical or different integers independently in a range of 0 to 4.

6. The composition according to claim 1, wherein the silica gel is a sol-gel material or a mesoporous silica gel.

7. The composition according to claim 6, wherein said divalent radical is selected from the group consisting of:

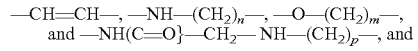

n, m, and p are identical or different integers independently in a range of 0 to 4.

8. A process for removing carbon monoxide from a gas mixture, comprising:
 i) contacting said gas mixture with a composition according to claim 1; and
 ii) adsorbing the carbon monoxide on the compound.

9. The process according to claim 8, wherein said compound is bonded to at least one component selected from the group consisting of: silica, sol-gel, and mesoporous silica.

10. The process according to claim 8, wherein the carbon monoxide is removed from a gas mixture comprising hydrogen.

* * * * *